US00PP36716P2

(12) United States Plant Patent
Meacham

(10) Patent No.: US PP36,716 P2
(45) Date of Patent: Jun. 3, 2025

(54) ***HEPTACODIUM* TREE NAMED 'JFS GM1HM'**

(50) Latin Name: *Heptacodium miconioides*
Varietal Denomination: JFS GM1HM

(71) Applicant: J. Frank Schmidt & Son Co., Boring, OR (US)

(72) Inventor: Guy E. Meacham, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 18/664,169

(22) Filed: May 14, 2024

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Zachariah Allan Kay
(74) *Attorney, Agent, or Firm* — Klarquist Sparkman, LLP

(57) ABSTRACT

A new variety of *Heptacodium miconioides* 'JFS GM1HM' with a unique combination of characteristics, combining a more upright narrower growth habit. Forming an upright oval canopy on a single central trunk, which begins flowering at an early age.

7 Drawing Sheets

Latin name of the genus and species of the plant claimed: *Heptacodium miconioides*.

Variety denomination: 'JFS GM1HM'.

BACKGROUND

*Heptacodium miconioides* (Seven Son Flower) is described as a large shrub or small tree. When grown from seed plants are very variable in both size and form but are generally multi trunked, and as wide and spreading as they are tall.

The goal was through the selection process to find a seedling that would be upright and narrow in habit with a single trunk making it more suitable for city street planting and landscape use with traits that could be reproduced through asexual propagation.

In May of 2012, 511 seedlings of *Heptacodium miconioides* were planted out in two rows in a nursery field in Canby Oregon. The seedlings were grown in Boring Oregon, from seeds purchased in the U.S.

In October 2014, the best 4 of these seedlings with the desired characteristics were selected. A single trunk, upright growth with good branching, leaf color and flower habit.

In the winter of 2014 these 4 trees were harvested and saved for replanting in a Nursery trial row in Boring Oregon. Here they were evaluated for a further 2 years assessing their characteristics and growth habit.

In the fall of 2016, the 2 best performing trees were named 'JFS GM1HM' and 'JFS GM2HM'. The other 2 trees were destroyed. In April 2017, these 2 trees were planted into a long term evaluation plot in Boring Oregon for continued evaluation.

In the summer of 2017, softwood cuttings were taken of 'JFS GM1HM' in Boring Oregon. 6 rooted cuttings were then planted out in a trial production row in 2018 in Boring Oregon to evaluate their growth habit for 3 years to see if these asexually produced plants exhibited the same growth habit and characteristics as the original plant. This process was repeated again in 2019 in Boring Oregon with 9 plants, and in 2020 in Boring Oregon with 25 plants.

All the plants from 2018 and 2019 were destroyed after harvest in 2021 and 2022. The 25 that were planted in 2020 were kept for use as future stock plants.

After these three consecutive trial plantings each lasting 3 years, it is confirmed that 'JFS GM1HM' has been asexually reproduced in Boring Oregon through succeeding asexual propagation, and the unique characteristics of 'JFS GM1HM' are stable and transferable through asexual propagation from summer softwood cutting propagation.

SUMMARY

This new cultivar possesses a unique combination of characteristics in that it combines a more upright branching narrow form when compared to the variability of the species. The cultivar also reliably flowers at a young age.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
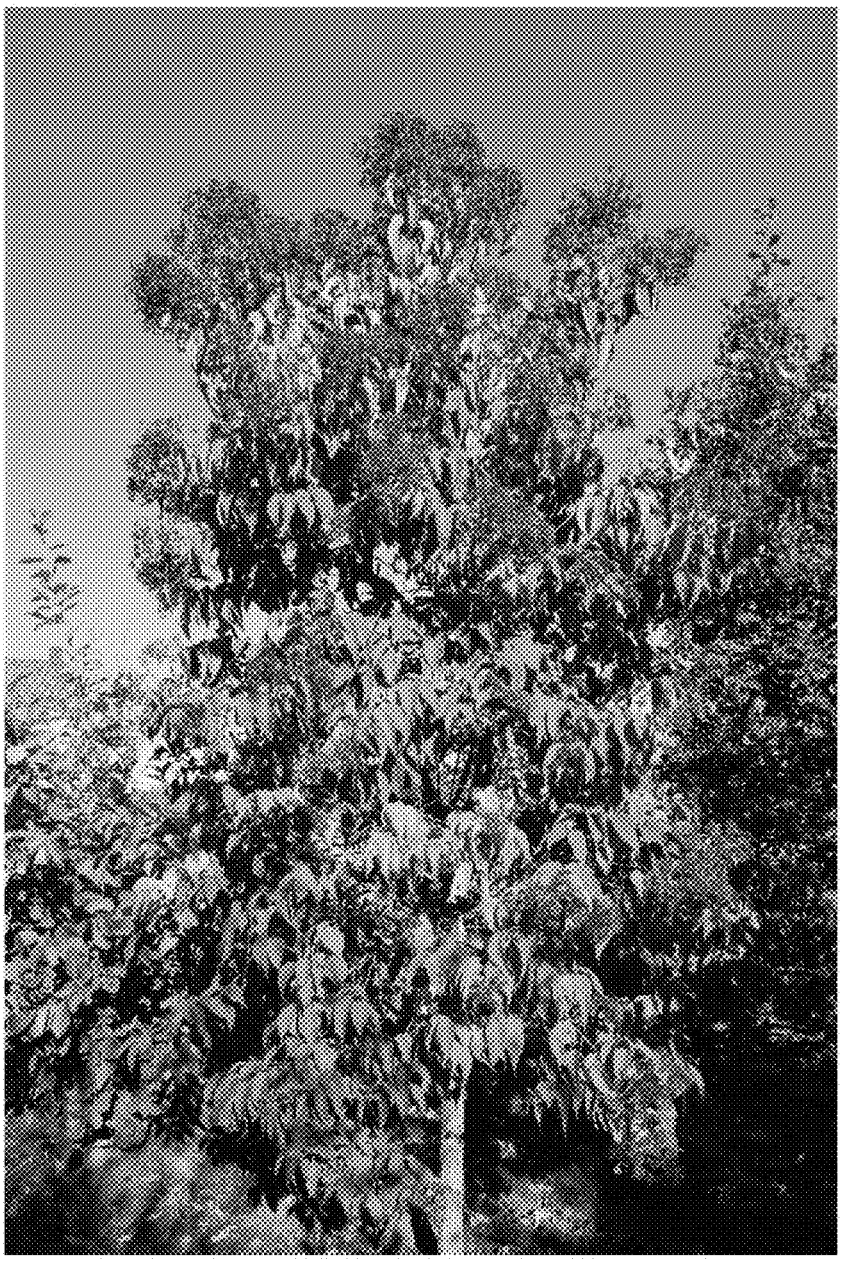
FIG. 1: Illustrates the original tree at 14 years of age in late summer with calyces.
Figure 2:
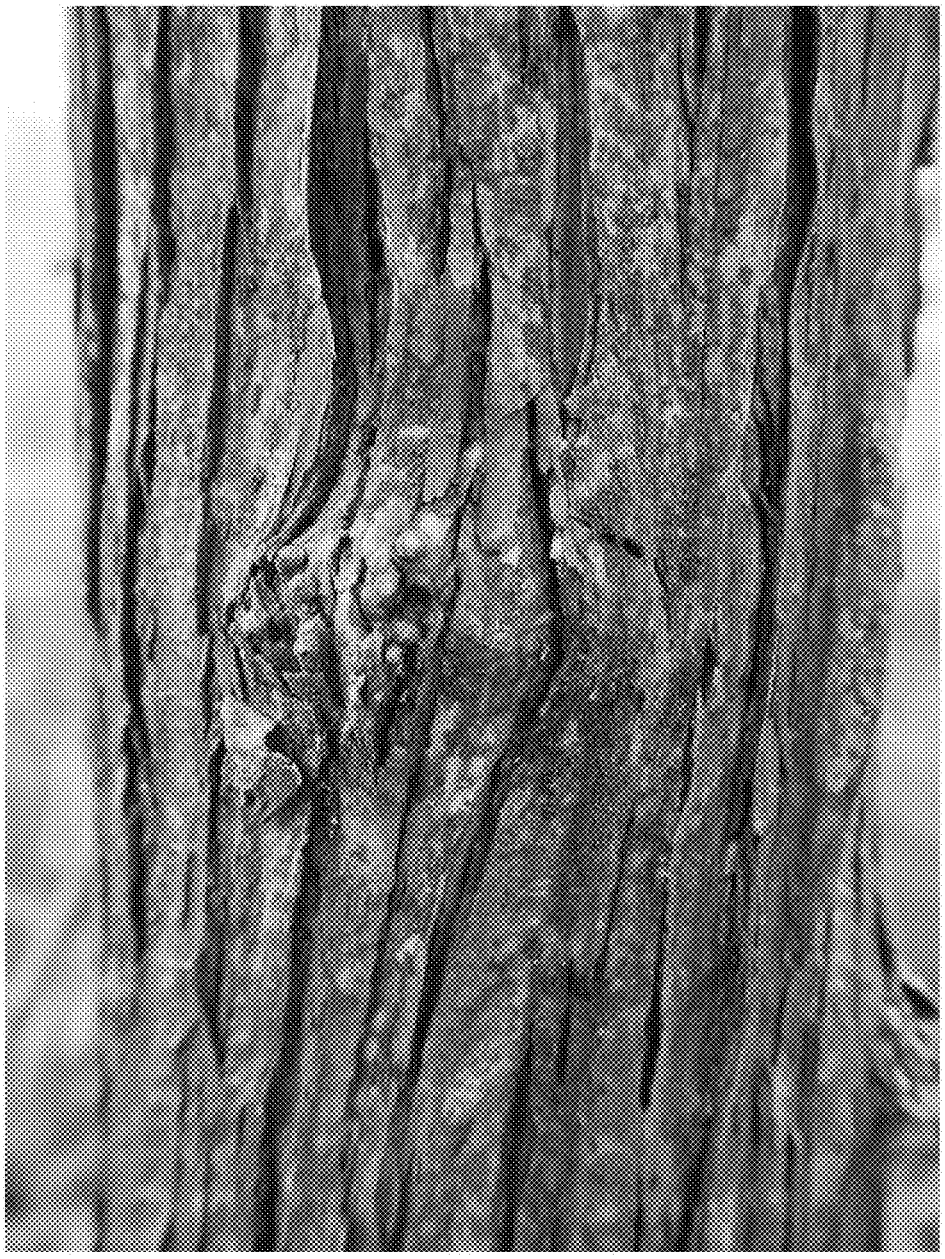
FIG. 2: Illustrates the original tree at 14 years of age showing the rough and exfoliating bark on the main trunk.
Figure 3:
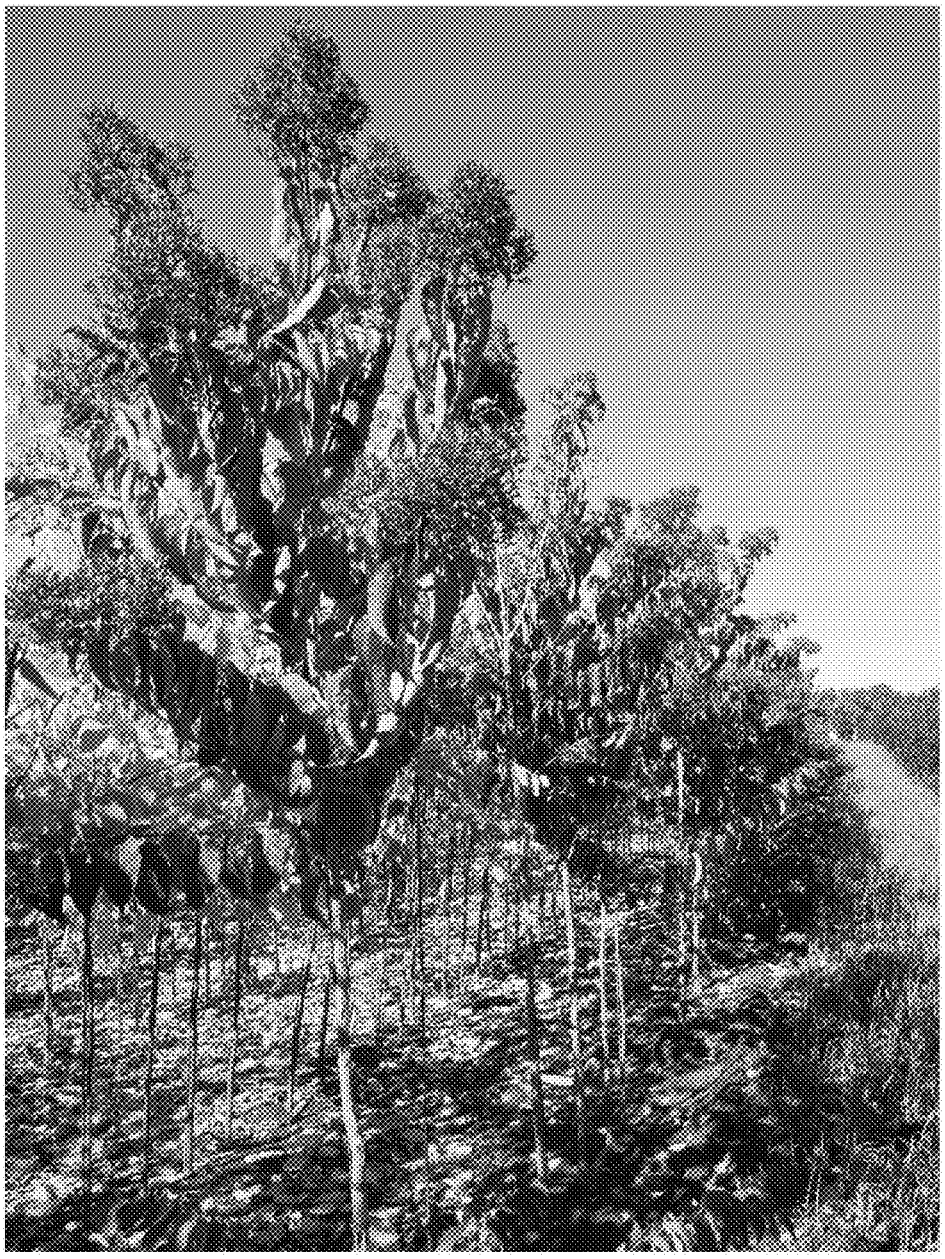
FIG. 3: Illustrates trees in a 2 year production row at the nursery.
Figure 4:
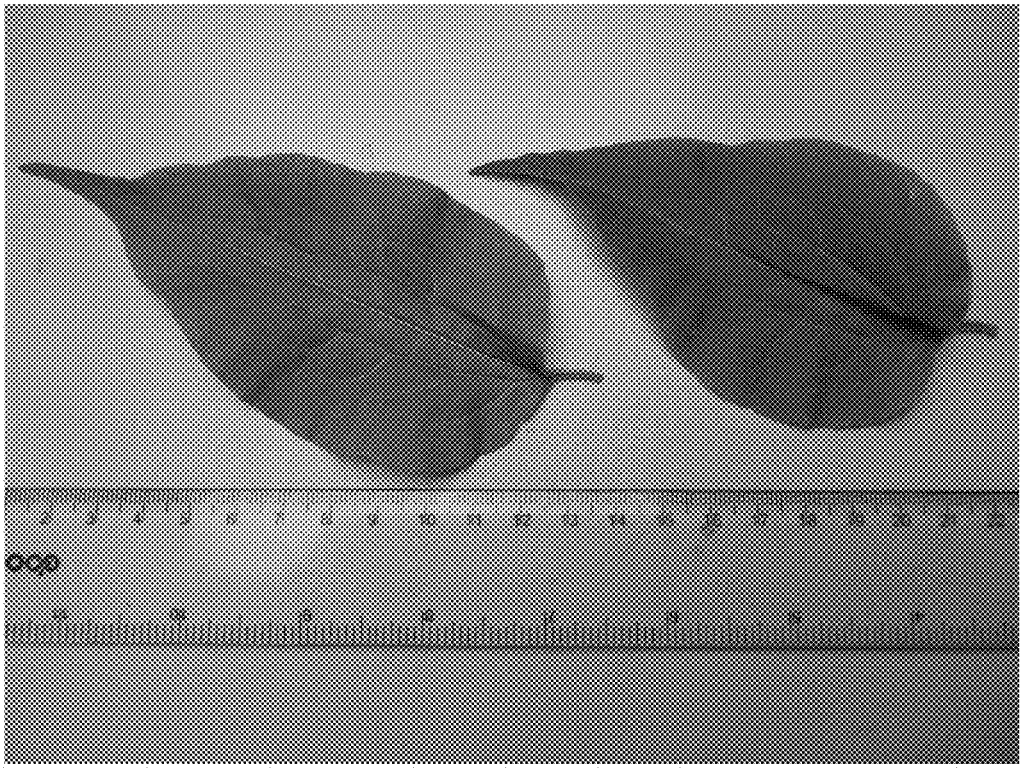
FIG. 4: Illustrates leaves in early Spring
Figure 5:
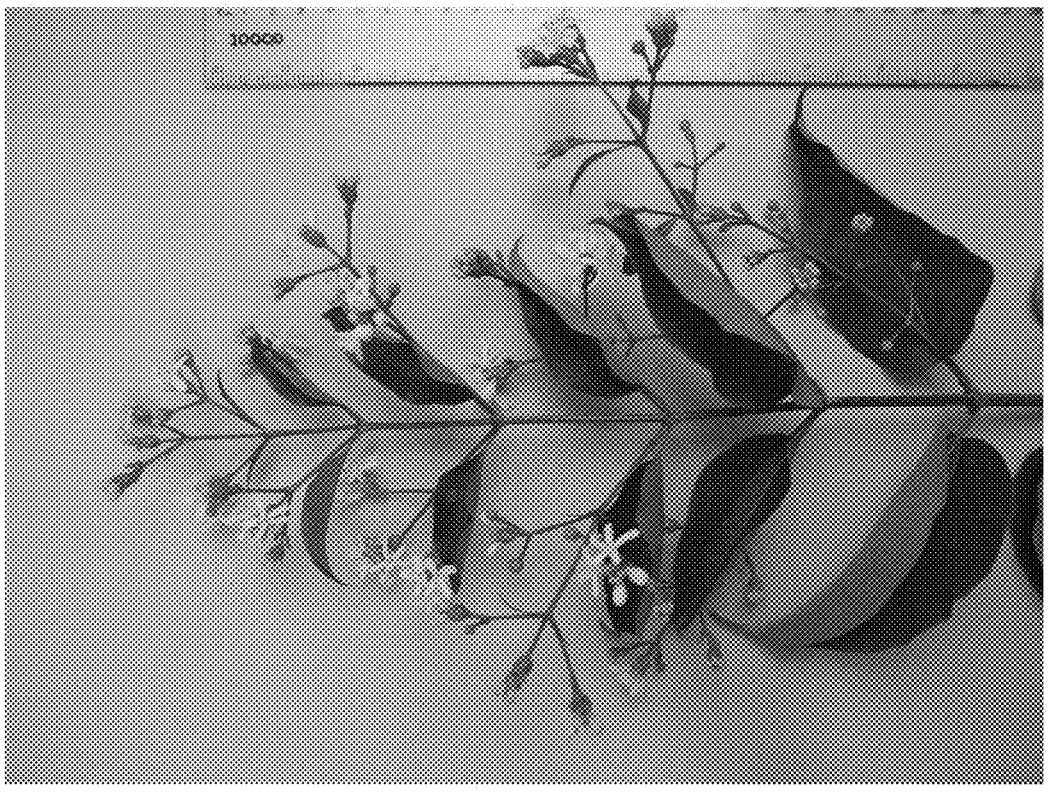
FIG. 5: Flowers on a grey board with scale showing size and color.
Figure 6:
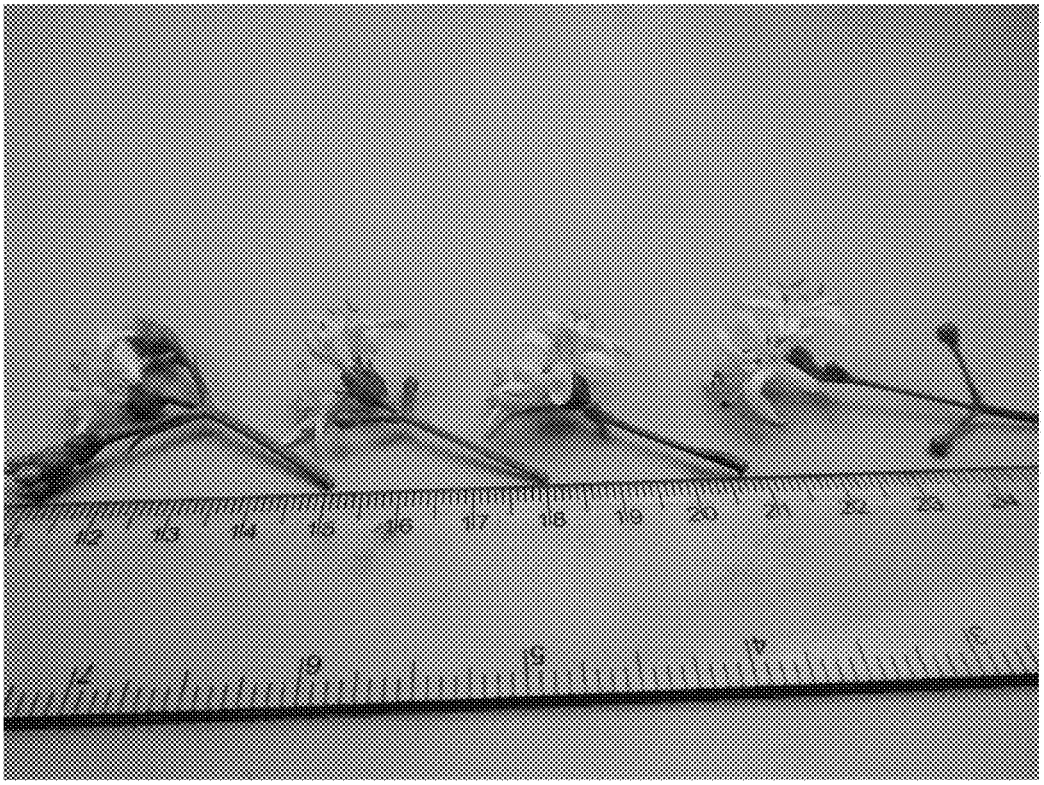
FIG. 6: Close-up of flowers on a grey board with scale showing size and color
Figure 7:
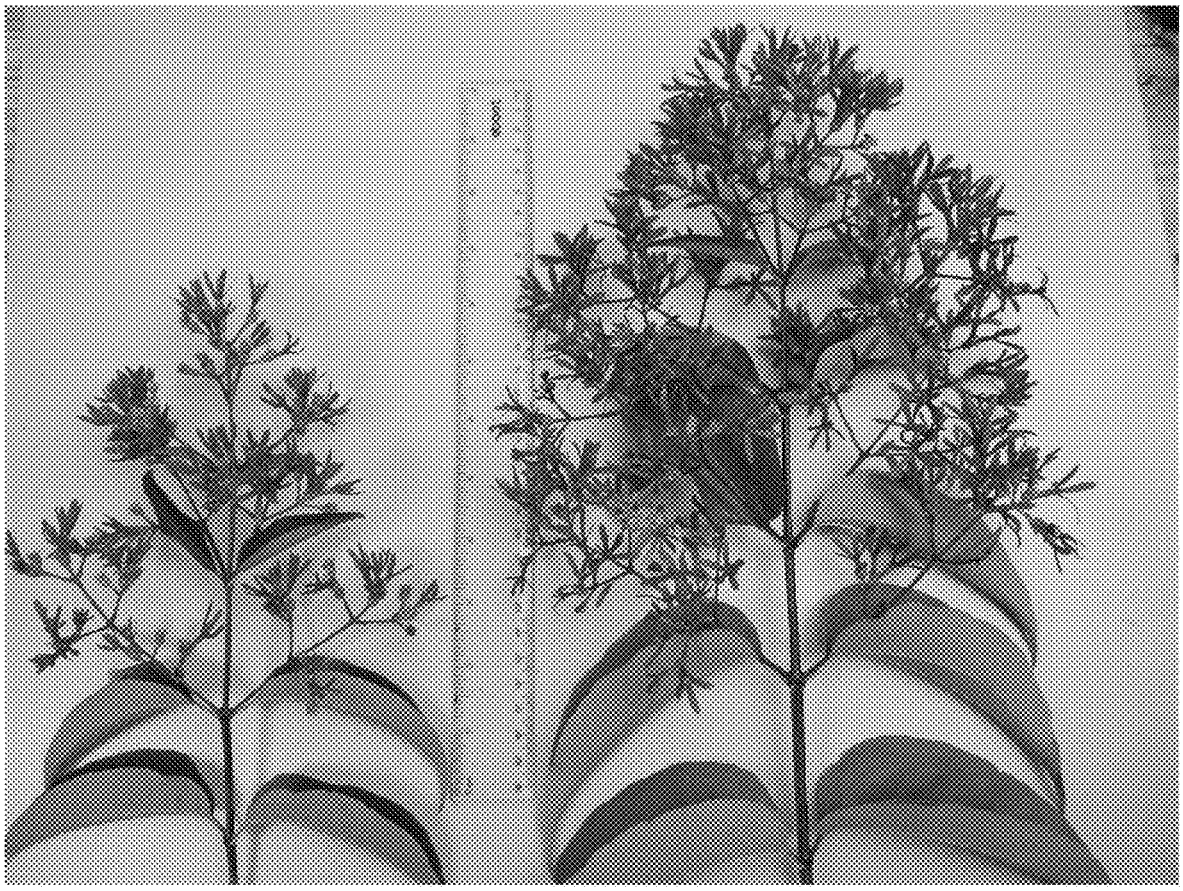
FIG. 7: Calyces on a grey board with scale showing size and fall colors.
Figure 8:
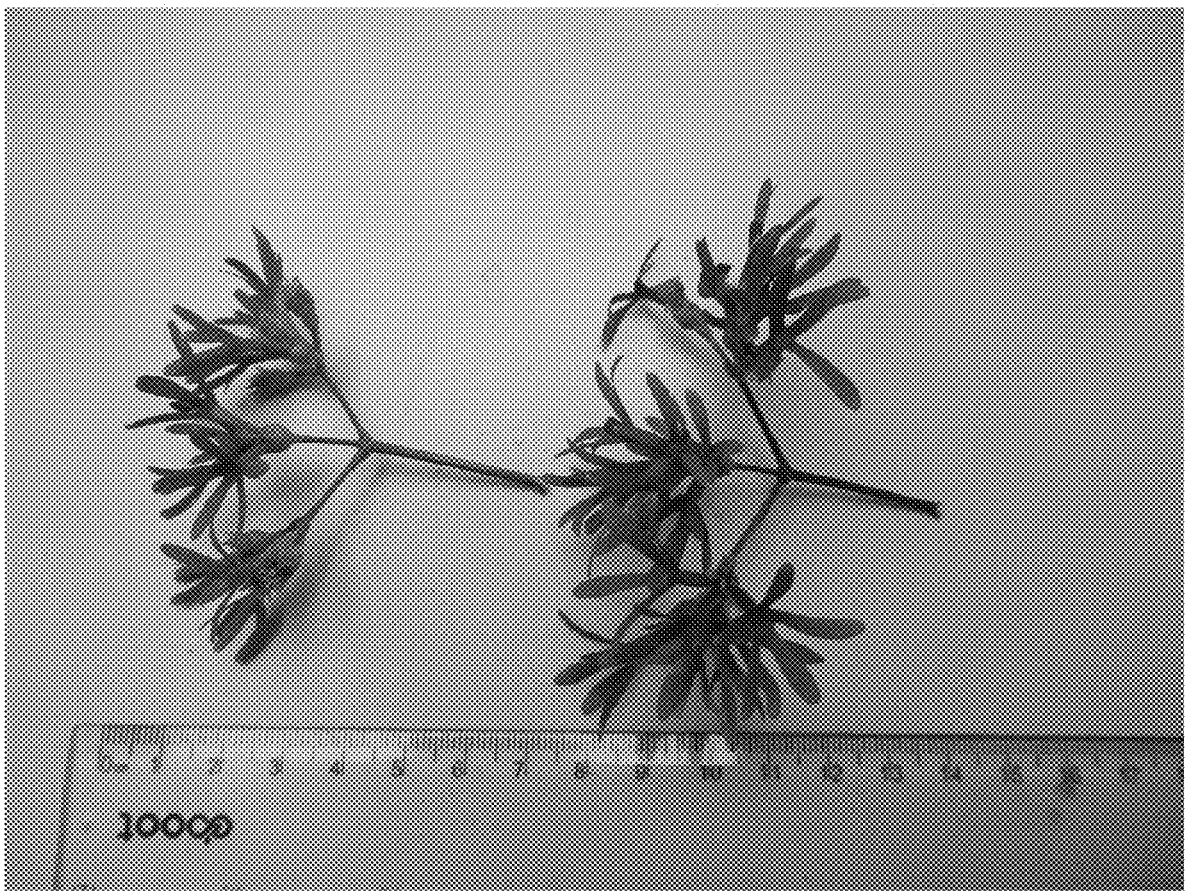
FIG. 8: Close-up of calyces on a grey board with scale showing size and fall colors.

The following detailed description of the 'JFS GM1HM' variety is based on observations of the original tree and one, and two, year old progeny. The observed progeny were trees which were growing in Boring, OR.

The following is a detailed description of the new *Heptacodium miconioides* 'JFS GM1HM' with color descriptions using terminology in accordance with The Royal Horticultural Society (London) Colour Chart©, 1986.

Scientific name: *Heptacodium miconioides* 'JFS GM1HM'.

Parentage:

*Seed parent*.—Unknown.

Tree:

*Overall shape*.—A small tree developing an Upright Oval canopy.

*Height*.—3.5 meters at 15 years of age.

*Width*.—1.5 meters at 15 years of age.

*Growth rate*.—Moderate when compared to other seedlings of *Heptacodium miconioides*.

*Trunk diameter*.—12.6 cm at 10 cm height, 9.5 cm at 1 meter, at 15 years of age.

*Trunk*.—Straight, strongly upright, single stem.

*Trunk bark texture*.—Rough and exfoliating.

*Trunk bark color*.—

*Immature bark color on 2 year old trees*.—Greyed-Orange 164B and Greyed-Orange 165B measured at 1 meter height in September.

*Mature bark color*.—Greyed-Orange 165B.

*Trunk lenticels*.—Not visible on trunk of original tree at 15 years of age.

*Primary branches*.—On the original tree at 15 years of age: Ascending, curving upward to a near vertical orientation from crotch angles that are generally 45° to 50°. Longest primary branches on the original tree at 15 years of age are about 1.5 meters long. On two year old trees in a nursery in Boring, OR, branches also curve upright producing a tree with an upright oval shape.

*Branch color*.—Young branches, during their first season of growth, are smooth barked, Greyed-Orange 165B and Greyed-Orange 167A as they mature in the fall. They become Greyed-Orange 174A and Greyed-Orange 175B in the winter.

*Branch lenticels*.—Not visible.

*Dormant buds*.—Imbricate, glabrous. Greyed-Orange 165C.

*Bud break*.—Bud break averages March 20th-25th under Boring, OR conditions.

*Internodes*.—Average length is 5-7 cm when measured on the mature branches of 2 year trees.

*Hardiness*.—Has tolerated field temperatures to 10 degrees F. without damage in Boring, OR and Canby, OR. It is believed to have Zone 5 cold hardiness similar to other plants of this species.

*Disease and insect resistance*.—Appears similar to the species with no differences noted.

Leaves: Except as otherwise noted, observations are from twenty vigorous growth leaves on trees grown in a nursery in Boring, OR.

*Arrangement*.—Opposite, single.

*Type*.—Simple, ovate.

*Texture*.—Slightly rough on the upper surface. Glabrous on the lower surface.

*Sheen*.—Dull on the upper and lower surfaces.

*Length*.—8 to 14 cm. on 1 and 2 year old tree.

*Width*.—4 to 6 cm. on 1 and 2 year old trees.

*Petioles*.—8 mm to 10 mm long×1 mm to 2 mm in diameter when measured on one and two year old trees. Color on the upper surface where exposed to sunlight is Yellow-Orange 22A.

*Margin*.—Entire.

*Tip*.—Acuminate.

*Base*.—Cordate to truncate.

*Stipules*.—None.

*Spring leaf color*.—Yellow Green 146C. Lower surface is 145C.

*Summer leaf color*.—

*Upper leaf surface*.—Green 143A and Green 139B.

*Lower leaf surface*.—Green 138C.

*Vein*.—Yellow-Green 145C.

*Fall leaf color*.—Individual leaves vary from Yellow 12A to Yellow-Orange 17A (including all colors in between) on top surface. From a distance, the overall color of the tree with foliage in mass appears similar to Yellow-Orange 15C.

*Timing of fall leaf color*.—Average dates for original tree in Boring, OR.

*Onset*.—October 25th.

*Peak*.—November 5th.

*Latest extent of fall color*.—November 15th.

*Defoliation*.—The tree is typically defoliated by November 30th.

*Persistence*.—The tree is deciduous.

Flowers:

*Overall*.—Flowers open in late Summer to early Fall in Boring OR.

*Shape*.—Flowers are born in Panicles.

*Flowers per inflorescence*.—30-40.

*Inflorescence size*.—Average 30 cm×25 cm.

*Individual flowers*.—Single, facing in all directions average 10 mm to 15 mm in size.

*Petals*.—Whorled, 5 per flower; they are near linear, entire with a rounded tip averaging 8 mm long×2 mm wide.

*Opened flower*.—White 155D.

*Sepals*.—Small until fall when they elongate and change color becoming attractive. In the fall the Sepals elongate to 10 to 15 mm and change from Green 145C to Red Purple 59C, 59D, and 60A becoming more prominent than the flowers.

*Arrangement*.—Whorled in 5.

*Anthers*.—1 mm long×0.5 mm wide, Brown 164C.

*Pollen*.—Yellow 13B.

*Flowering date*.—Based on 2023 data for the original tree in Boring, Oregon. First bloom: September 20.Peak bloom: October 5.End of bloom: October 20.

Fruit: Due to the late flowering of *Heptacodium miconioides* in Oregon fruit and seed rarely form. Neither has been observed on 'JFS GM1HM'.

COMPARISON TO THE SPECIES

The new variety 'JFS GM1HM' has a much tighter and upright branch habit that develops a canopy that is more upright oval than the species. Branches curve upward close to the main trunk and are less spreading than the species. Typical seedlings of the species have a far more variable and spreading form.

Data in the following table was collected from trees growing in a nursery in Boring, Oregon.

TABLE 1

| Feature: | 'JFS GM1HM' | 'JFS GM2HM' | Seedling *Heptacodium miconioides* |
|---|---|---|---|
| Typical canopy shape of tree at 14 years | 3.5 m × 1.5 m | 3.5 m × 2.5 m | 3.5 m × 3.0 m |
| Branch angle degrees from vertical, 50 cm proximal to tip of mid-canopy branches | 45° to 50° | 60° to 70° | 65° to 75° |
| Summer leaf color | Green 138B or Green 139C | Green 142A or Green 142B | Green 145A or Green 146D |
| Sepals | 10-15 mm long Red Purple | 10-15 mm long Red Purple | 8-12 mm long Red Purple |

TABLE 1-continued

| Feature: | 'JFS GM1HM' | 'JFS GM2HM' | Seedling *Heptacodium miconioides* |
|---|---|---|---|
| | 59C or Red Purple 60A | 60C or Red Purple 60D | 63A or Red Purple 63C |

COMPARISON TO ANOTHER CULTIVAR

The new variety 'JFS GM1HM' can easily be distinguished from other cultivara of *Heptacodium miconioides* by its more upright narrow oval form.

TABLE 2

| Feature: | 'JFS GM1HM' | 'SMNHMRF' U.S. Plant Pat. No. 30,763 |
|---|---|---|
| Typical Canopy Shape | 3.5 m - × 1.5 m | 4.5 m × 1.8-3.0 m |
| Trunk | Single trunk. | Multi trunked |
| Summer leaf color | Green 138B and Green 139C | Green 143A |
| Ornamental Sepals | 10-15 mm long Red Purple 59C, 59D, and 60A | 10 mm Red Purple 60C |

I claim:

1. A new and distinct variety of *Heptacodium miconioides* tree named 'JFS GM1HM', substantially as illustrated and described herein.

* * * * *